(12) United States Patent
Lorant

(10) Patent No.: US 6,638,519 B1
(45) Date of Patent: Oct. 28, 2003

(54) COMPOSITION FOR TOPICAL APPLICATION COMPRISING A SUGAR AND ITS COSMETIC USES

(75) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/707,952

(22) Filed: Nov. 8, 2000

(30) Foreign Application Priority Data

Nov. 8, 1999 (FR) .............................................. 99 13990

(51) Int. Cl.[7] .............................. A61K 7/00; A61K 7/48; A61K 9/10; A61K 9/107; A61K 31/70
(52) U.S. Cl. ........................ 424/401; 424/59; 424/404; 424/64; 514/53; 514/724; 514/844; 528/15
(58) Field of Search .......................... 424/401, 59, 484, 424/64; 514/53, 724, 844; 528/15

(56) References Cited

U.S. PATENT DOCUMENTS

| | | | |
|---|---|---|---|
| 5,266,321 A | | 11/1993 | Shukuzaki et al. |
| 5,412,004 A | * | 5/1995 | Tachibana et al. ............. 524/27 |
| 5,626,853 A | * | 5/1997 | Bara et al. ................... 424/401 |
| 5,928,660 A | * | 7/1999 | Kobayashi et al. .......... 424/401 |
| 6,306,411 B1 | * | 10/2001 | Jager Lezer ................. 424/401 |
| 6,403,704 B1 | * | 6/2002 | Bara .......................... 424/401 |

FOREIGN PATENT DOCUMENTS

| | | | |
|---|---|---|---|
| EP | 240349 A2 | | 10/1987 |
| EP | 0 545 002 A1 | | 6/1993 |
| EP | 0829253 A2 | | 3/1998 |
| EP | 0855178 A2 | | 7/1998 |
| EP | 1023893 A1 | | 8/2000 |
| EP | 1051968 A2 | | 11/2000 |
| EP | 1064930 A1 | | 1/2001 |
| JP | 410114626 A | * | 5/1998 |
| WO | WO 97/32561 | | 9/1997 |
| WO | WO 00/78279 A1 | | 12/2000 |

OTHER PUBLICATIONS

*Methyl Glucoside Products: Multifunctional ingredients that are naturals for today's personal care products*, Amerchol, Sep. 1992.

Dow Corning® 9040 Silicone Elastomer Blend, 1998 Dow Corning Coporation.

*Lexikon der Hilfsstoffe für Phrmazie, Kosmetik und angrenzende Gebiete*, Dr. Herbert P. Fiedler.

Opposition related to EP1097703B1 (8 pages).

* cited by examiner

Primary Examiner—Frederick Krass
Assistant Examiner—Clinton Ostrup
(74) *Attorney, Agent, or Firm*—Oblon, Spivak, McClelland, Maier & Neustadt, P.C.

(57) ABSTRACT

The first embodiment of the present invention provides a composition, which includes:

at least one aqueous phase that includes an aqueous suspension of particles of an at least partially crosslinked organopolysiloxane elastomer; and at least one sugar or sugar derivative. Other embodiments of the invention provide for the use of the above-described composition. Another embodiment of the invention provides a method selected from the group including treating, protecting, caring for, removing make-up from, and cleaning at least one selected from the group including the skin, lips and hair, and combinations thereof, which method includes applying the above-described composition to the skin, lips or hair. Another embodiment of the invention provides a method for treating or caring for at least one selected from the group including dry skin, dry lips, sensitive skin, and combinations thereof which includes applying to at least one selected from the group including dry skin, dry lips, sensitive skin, and combinations thereof in need thereof the above-described composition. Another embodiment of the invention provides a method for preparing an emulsion composition, which method includes separately heating an oily phase and an aqueous phase, the aqueous phase including an aqueous suspension of particles of an at least partially crosslinked organopolysiloxane elastomer and at least one sugar or sugar derivative, to obtain a heated oily phase and a heated aqueous phase; admixing the heated oily phase and the heated aqueous phase and emulsifying, to obtain the emulsion composition. Another embodiment of the invention provides a method for reducing or eliminating the sticky feel of a composition that includes at least one sugar or sugar derivative, which method includes introducing into the composition an aqueous suspension of particles of an at least partially crosslinked organopolysiloxane elastomer.

34 Claims, No Drawings

COMPOSITION FOR TOPICAL APPLICATION COMPRISING A SUGAR AND ITS COSMETIC USES

BACKGROUND OF THE INVENTION

1. Field of the Invention

The present invention relates to a composition that includes a sugar and/or a sugar derivative and an aqueous suspension of particles of an at least partially crosslinked organopolysiloxane elastomer. The invention also relates to the uses, in particular cosmetic uses, of this composition, especially for caring for, cleaning and/or removing makeup from the skin, mucous membranes, eyes and/or hair. The invention also relates to the use of an aqueous suspension of particles of organopolysiloxane, in a composition that includes at least one sugar and/or one sugar derivative, in order to eliminate the sticky feel due to this sugar or sugar derivative.

2. Discussion of the Background

It is common practice to introduce sugars or sugar derivatives into current cosmetic compositions in order to impart a better and more comfortable feeling thereto during use (softness, emollience and others), owing to the fact that these compounds contribute in particular softness and better tolerance of the products. Thus, sugar-derived surfactants are softer and less irritating than conventional surfactants. Furthermore, sugars have good moisturizing properties and may be incorporated in cosmetic compositions as moisturizers.

Sugars and sugar derivatives, however, have the disadvantage of imparting a sticky character to the compositions that contain them.

EP-A-545,002, WO-A-97/32561 and U.S. Pat. No. 5,266,321 disclose cosmetic compositions that contain sugar esters and also organopolysiloxane elastomeric particles. The organopolysiloxane elastomer particles disclosed in these documents are in the form of oily gels and in particular silicone gels in which the particles swell. The oily gels are introduced into the oily phase and, accordingly, do not impart a sensation of freshness when applied to the skin. In addition, the compositions disclosed in the references do not reduce the sticky effect of sugars or sugar derivatives.

The need thus remains for a composition for topical application, in particular a cosmetic composition, which contains a sugar and/or a sugar derivative, but which does not confer a sticky feeling on the skin.

SUMMARY OF THE INVENTION

Accordingly, one object of the present invention is to provide a composition that contains a sugar and/or a sugar derivative, but which does not impart a sticky feeling to the skin.

Another object of the present invention is to provide a composition for topical application, and in particular a cosmetic composition, that contains a sugar and/or sugar derivative, but which does not impart a sticky feeling to the skin.

These and other objects have been attained by the present invention, the first embodiment of which provides a composition, which includes:

at least one aqueous phase that includes an aqueous suspension of particles of an at least partially crosslinked organopolysiloxane elastomer; and at least one sugar or sugar derivative.

Another embodiment of the invention provides a cosmetic, which includes the above-described composition and a physiologically acceptable medium.

Another embodiment of the invention provides an emulsion selected from the group including an O/W emulsion, W/O emulsion, W/O/W triple emulsion, O/W/O triple emulsion, which includes the above-described composition, an oily phase, and, optionally, one or more emulsifiers.

Another embodiment of the invention provides a cosmetic, which includes comprising the above-described emulsion and a physiologically acceptable medium.

Another embodiment of the invention provides a method selected from the group including treating, protecting, caring for, removing make-up from, and cleaning at least one selected from the group including the skin, lips and hair, and combinations thereof, which method includes applying the above-described composition to the skin, lips or hair.

Another embodiment of the invention provides a method for treating or caring for at least one selected from the group including dry skin, dry lips, sensitive skin, and combinations thereof which includes applying to at least one selected from the group including dry skin, dry lips, sensitive skin, and combinations thereof in need thereof the above-described composition.

Another embodiment of the invention provides a method for preparing an emulsion composition, which includes:

separately heating an oily phase and an aqueous phase, the aqueous phase including an aqueous suspension of particles of an at least partially crosslinked organopolysiloxane elastomer and at least one sugar or sugar derivative, to obtain a heated oily phase and a heated aqueous phase;

admixing the heated oily phase and the heated aqueous phase and emulsifying, to obtain the emulsion composition.

Another embodiment of the invention provides a method for reducing or eliminating the sticky feel of a composition that includes at least one sugar or sugar derivative, which method includes introducing into the composition an aqueous suspension of particles of an at least partially crosslinked organopolysiloxane elastomer.

DESCRIPTION OF THE PREFERRED EMBODIMENTS

Various other objects, features and attendant advantages of the present invention will be more fully appreciated as the same becomes better understood from the following detailed description of the preferred embodiments of the invention.

Surprisingly, the present inventor has found that it is possible to suppress the sticky feel on the skin of a composition comprising a sugar and/or a sugar derivative in part by introducing an aqueous suspension of particles of an at least partially crosslinked organopolysiloxane elastomer.

EP-A-545,002, WO-A-97/32561 and U.S. Pat. No. 5,266,321 disclose cosmetic compositions that contain sugar esters and also organopolysiloxane elastomer particles. However, the organopolysiloxane elastomer particles disclosed in these documents are in the form of oily gels and in particular silicone gels in which the particles swell, whereas the particles used according to the present invention are dispersed in an aqueous medium in which they do not swell. The oily gels disclosed in the abovementioned documents are introduced into an oily phase and not into an aqueous phase and accordingly, they do not give a sensation of freshness when applied on the skin. In addition, they do not contribute to suppressing the sticky effect of sugars or sugar derivatives, in contrast to the particles in aqueous suspension according to the present invention.

A preferred embodiment of the invention consequently relates to a composition that includes, in a physiologically acceptable medium, at least an aqueous phase, at least one sugar and/or one sugar derivative and an aqueous suspension of particles of at least partially crosslinked organopolysiloxane elastomer, the suspension being present in the aqueous phase of the composition.

The term "physiologically acceptable" is understood to mean in the present application a medium compatible with the skin, eyes and keratinous fibers of human beings.

The term "sugar" is understood to mean in the present application compounds which have one or more alcohol functional groups, with or without an aldehyde or ketone functional group, and which include at least 4 carbon atoms and preferably from 5 to 6 carbon atoms.

It is believed that because the particles of at least partially crosslinked organopolysiloxane elastomer are in aqueous suspension and are thus introduced in an aqueous phase, the composition that results is much fresher and more pleasant on application than if these particles were in the oily phase. This freshness effect is particularly noticeable in the case of compositions that contain an oily phase and in particular in the case of oil-in-water (O/W) or water-in-oil (W/O) emulsions.

It is believed that the presence of the aqueous suspension of particles of organopolysiloxane elastomer in the composition makes it possible in part to prevent, reduce or eliminate the sticky effect contributed by the sugar or the sugar derivative.

Consequently, a preferred embodiment of the present invention also relates to the use of an aqueous suspension of particles of an at least partially crosslinked organopolysiloxane elastomer, in a composition that contains at least one sugar and/or one sugar derivative, in order to eliminate the sticky feel due to this sugar and/or sugar derivative.

The term "elastomer" is understood to mean in the present application a flexible and deformable material having viscoelastic properties and preferably having the consistency of a sponge or of a flexible sphere. The modulus of elasticity of an elastomer is such that it is resistant to deformation and has a limited ability to expand and to contract. An elastomer is capable of returning to its original shape after it has been stretched. This elastomer is preferably formed of polymeric chains of high molecular weight, the mobility of which is limited by a uniform network of crosslinking points.

The organopolysiloxane elastomers of the composition of the invention do not dry out the skin and contribute to good cosmetic properties such as softness and mattness. These elastomers in part result in compositions which are comfortable on application, which spread well, which are soft, non-greasy and non-sticky to the touch.

The elastomers of the invention are preferably provided in the form of an emulsified gel that includes an organopolysiloxane elastomer with a three-dimensional structure dispersed in water. The dispersion (or suspension) of the particles is preferably homogeneous. These elastorners are preferably chosen from the crosslinked polymers disclosed in JP-A-10/175816 (corresponding to U.S. Pat. No. 5,928, 660) the entire contents of each of which are hereby incorporated by reference. According to this application, they are preferably obtained by an addition and crosslinking reaction, in the presence of a catalyst and preferably of the platinum type or platinum group, of at least:

(a) one organopolysiloxane (i) having at least two vinyl groups in the α, ω-position of the silicone chain per molecule; and (b) one organosiloxane (ii) having at least one hydrogen atom bonded to a silicon atom per molecule.

Preferably, the organopolysiloxane (i) is chosen from polydimethylsiloxanes and is more preferably an α, ω-dimethylvinylpolydimethylsiloxane.

The aqueous suspension of organopolysiloxane elastomer particles which is used in the composition according to the invention is preferably obtained as follows:

(a) mixing the organopolysiloxane (i) and the organosiloxane (ii);

(b) adding the aqueous phase that contains an emulsifier to the mixture from stage (a);

(c) emulsifying the aqueous phase and the mixture;

(d) adding warm water to the emulsion from stage (c); and (e) polymerizing the organopolysiloxane (i) and the organosiloxane (ii) in an emulsion in the presence of a platinum or platinum group catalyst.

Preferably, stage (c) is carried out in the presence of a nonionic emulsifier.

In this process, the water is preferably added at a temperature of approximately greater than 30° C., more preferably of 35° C. to 90° C., and most preferably of approximately 40 to 60° C. After stage (e), it is possible to dry the particles obtained in order to evaporate therefrom all or a portion of the trapped water.

The organopolysiloxanes are preferably in the form of solid deformable particles having a degree of hardness measurable with a Shore A durometer (according to ASTM Standard D2240) at room temperature or with the Japanese method JIS-A. This hardness can be measured on an elastomer block prepared as follows: mixing the organopolysiloxane (i) and the organosiloxane (ii); removing the air from the mixture; molding and vulcanizing in an oven at 100° C. for 30 minutes; cooling to room temperature and then measuring the hardness. The relative density is also determined on this elastomer block.

The Shore hardness is preferably less than or equal to 80 and more preferably less than 65. The organopolysiloxanes of the composition of the invention preferably include, for example, those sold under the names BY 29–122 and BY 29–119 by the company Dow Coming Electric. It is also possible to use a mixture of these commercial products. A block of elastomers according to the product BY 29–122 exhibits a hardness of 7 and, according to the product BY 29–119, a hardness of 30. The relative density is from 0.97 to 0.98. The suspensions with the names BY 29–122 and BY 29–119 comprise approximately 63% by weight of organopolysiloxane elastomer particles(thus approximately 63% of active material) with respect to the total weight of the suspension.

In particular, the organopolysiloxane elastomer particles (as active material) have a size ranging from 0.1 to 500 μm and better still from 3 to 200 μm. These ranges include all values and subranges therebetween, including 1 μm, 50 μm, 75 μm, 100 μm and 300 μm. These particles can be spherical, flat or amorphous with, preferably, a spherical shape.

Preferably, the organopolysiloxane elastomers in accordance with the invention are partially or completely crosslinked and have a three-dimensional structure. The degree of crosslinking is easily determined by one of ordinary skill in the art, and can preferably range from greater than one to 100%, more preferably from greater than or equal to 5% to less than or equal to 85%, and most preferably greater than or equal to 40% to less than or equal to 75%. These ranges include all values and subranges therebetween, including 2%, 9%, 10%, 25%, 30%, 45%, and 65%.

As indicated in the process described above, in order for these organopolysiloxane particles to be more stably dispersed in water, they can be combined with one or more nonionic, cationic or anionic emulsifiers with an HLB (hydrophilic-lipophilic balance) greater than or equal to 8. More preferably, the HLB value is greater than or equal to 9, and most preferably greater than or equal to 10. The proportion of emulsifiers in the aqueous suspension preferably ranges from 0.1 to 20 parts by weight per 100 parts by weight of the aqueous organopolysiloxane elastomer suspension and better still from 0.5 to 10 parts by weight.

Preferably, these organopolysiloxane elastomer particles may be combined, in the aqueous suspension, with fatty substances and more preferably with oils, such as those disclosed in JP-A-10/175816, waxes or gums which are solid at room temperature, pasty fatty substances, of animal, vegetable, mineral or synthetic origin, or their mixtures, and inorganic powders, such as those disclosed in this document.

The organopolysiloxane elastomer particles are preferably present in the composition of the invention in an amount of active material ranging, for example, from 0.1 to 30% by weight and preferably from 0.5 to 20% by weight with respect to the total weight of the composition. These ranges include all values and subranges therebetween, including 0.2%, 0.9%, 1%, 5%, 10%, 15% and 25%.

Preferable sugars, which can be used in the composition of the invention include, for example, sucrose, glucose, galactose, ribose, fucose, trehalose, maltose, fructose, mannose, arabinose, xylose, lactose, their derivatives, in particular their alkylated derivatives, such as methylated derivatives, for example methylglucose, as well as compounds that contain one or more sugars, and their mixtures.

Preferable compounds that contain one more sugars or a mixture of sugars include natural compounds, such as honey, and polymers, such as, for example, the product sold under the name "Fucogel 1000" by the company Solabia (CTFA name, Biosaccharide gum-1), a polymer comprising fucose, galactose and galacturonic acid.

Preferable sugar derivatives which can be used in the composition of the invention include sugar fatty esters, which are optionally oxyalkylenated (oxyethylenated and/or oxypropylenated) or polyglycerolated, and sugar fatty ethers. These compounds can be used in particular as emulsifying surfactants. Mixtures of these derivatives are possible.

Preferable esters of fatty acid and sugar include esters or mixtures of esters of linear or branched and saturated or unsaturated $C_{12}$ to $C_{22}$ fatty acids and of sucrose, maltose, glucose, fructose, mannose, galactose, arabinose, xylose, lactose, trehalose or methylglucose. These esters are preferably chosen from mono-, di-, tri- and tetraesters, polyesters and their mixtures. The $C_{12}$ to $C_{22}$ fatty acids includes $C_{12}$, $C_{13}$, $C_{14}$, $C_{15}$, $C_{16}$, $C_{17}$, $C_{18}$, $C_{19}$, $C_{20}$, $C_{21}$ and $C_{22}$ in any subrange or combination. These esters are preferably chosen from stearates, behenates, cocoates, arachidonates, palmitates, myristates, laurates, carprates, oleates, laurates and their mixtures.

Sucrose esters are also preferably used. Preferable sucrose esters include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose polyesters, such as sucrose pentaoleate, hexaoleate, heptaoleate or octooleate, and mixed esters, such as sucrose palmitate/stearate. Mixtures are possible.

Preferable esters or mixtures of esters of fatty acid and of sucrose include those sold by the company Crodesta under the names F160, F140, F110, F90, F70 or SL40, respectively denoting the sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, of 39% monoester and 61 % di-, tri- and tetraester, or sucrose monolaurate. Use may also be made of those sold by the company Mitsubishi under the name Ryoto Sugar esters, for example under the reference B370 corresponding to sucrose behenate formed of 20% monoester and 80% di-, tri- and polyester. Mention may also be made of the sucrose mono- and dipalmitate/stearate sold by the company Goldschmidt under the name "Tegosoft PSE". Use may also be made of a mixture of these various products.

The sugar ester can also be present in admixture with another compound not derived from sugar; and a preferred example includes the mixture of sorbitan stearate and of sucrose cocoate sold under the name "Arlatone 2121" by the company ICI.

Other preferable sugar esters include, for example, glucose trioleate, galactose di-, tri-, tetra- or pentaoleate, arabinose di-, tri- or tetralinoleate or xylose di-, tri- or tetralinoleate. Mixtures are possible.

Other preferable esters or mixtures of esters of fatty acid and of methylglucose include the distearate of methylglucose and of polyglycerol-3 sold by the company Goldschmidt under the name of Tegocare 450. Mention may also be made of glucose or maltose monoesters, such as methyl O-hexadecanoyl-6-D-glucoside and (lacuna) O-hexadecanoyl-6-D-maltose.

Preferable oxyethylenated esters of fatty acid and of sugar include oxyethylenated (20 EO) methylglucose sesquistearate, such as the product sold under the name "Glucamate SSE20", by the company Amerchol.

Preferable ethers of fatty alcohol and of sugar which can be used as surfactants in the composition include ethers or mixtures of ethers of $C_8$–$C_{22}$ fatty alcohol and of glucose, maltose, sucrose or fructose and ethers or mixtures of ethers of $C_4$–$C_{22}$ fatty alcohol and of methylglucose. These are in particular alkylpolyglucosides.

Preferably, the $C_8$–$C_{22}$ or $C_{14}$–$C_{22}$ fatty alcohols forming the fatty unit of the sugar ethers include a saturated or unsaturated branched or linear alkyl chain respectively containing from 8 to 22 or from 14 to 22 carbon atoms. This includes $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$ in any sub the fatty alcohol is a liner fatty alcohol. Preferably, the fatty unit of the ethers includes any of decyl, cetyl, behenyl, arachidyl, stearyl, palmityl, myristyl, lauryl, capryl or hexadecanyl units and their mixtures, such as cetearyl.

Preferable ethers of fatty alcohol and of sugar include alkylpolyglucosides, such as decylglucoside and laurylglucoside, sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tegocare CG90 by the company Goldschmidt and under the name Emulgade KE3302 by the company Henkel, and arachidylglucoside, for example in the form of the mixture of arachidyl and behenyl alcohols and of arachidylglucoside sold under the name Montanov 202 by the company Seppic. Mention may also be made of the alkylpolyglycosides with an HLB (hydrophilic-lipophilic balance) of less than 7, which can be used in particular in W/O emulsions, such as isostearylglucoside, optionally as a mixture with isostearyl alcohol, sold, for example, under the name Montanov W018 by the company Seppic, and oleylglucoside, optionally as a mixture with oleyl alcohol, sold by the company Seppic. According to a particularly preferable embodiment of the invention, the mixture of the alkylpolyglucoside as defined above with the corresponding fatty alcohol can be in the form of a self-emulsifying composition, as disclosed, for example, in the document WO-A-92/06778, the entire contents of which are hereby incorporated by reference.

The sugars or sugar derivatives can be introduced into the aqueous phase or an oily phase of the composition of the invention. The sugars are preferably introduced into the aqueous phase, however. The sugar derivatives may be introduced into the aqueous phase or an oily phase according to their hydrophilic or lipophilic natures.

The amount of sugar(s) and/or sugar derivative(s) present in the composition of the invention is not particularly limited and can vary to a large extent according to the desired goal. Preferably, the sugar(s) and/or sugar derivative(s) may be present in an amount ranging from 0.1 to 20% by weight, more preferably 0.2 to 15% by weight, and most preferably from 0.5 to 10% by weight with respect to the total weight of the composition. These ranges include all values and subranges therebetween, including 0.15%, 1%, 2.5%, 5%, 7%, 12%, and 18%.

The composition according to the invention is particularly suitable for topical use and preferably forms the basis either alone or as part of a cosmetic and/or dermatological composition.

Preferably, the composition according to the invention may be provided in any pharmaceutical dosage form conventionally used in the cosmetic and dermatological fields and it can preferably take the form of an optionally gelled aqueous solution, of an aqueous gel, of a dispersion, of an emulsion obtained by dispersion of an oily phase in an aqueous phase (O/W) or vice versa (W/O), or of a triple emulsion (W/O/W or O/W/O). They can also be in a vectorized form, such as, for example, in the form of nanocapsules, of liposomes, of nanoemulsions or of oleosomes. These compositions are prepared according to the usual methods.

According to a preferred embodiment of the invention, the composition is in the form of an O/W or W/O emulsion and preferably of an O/W emulsion.

When the composition is an emulsion, the latter preferably includes at least one oil and optionally an appropriate emulsifier, which emulsifier is more preferably a sugar derivative.

The nature of the oily phase participating in the composition of the emulsions is particularly limited and is preferably composed of any fatty substance and more preferably oil conventionally used in the cosmetics and dermatological fields.

Preferable oils which can be used in the emulsion of the invention include vegetable oils (for example of apricot kernel, jojoba, avocado, sesame, sunflower, maize, soybean, safflower, grape seed, liquid fraction of karite butter or plant perhydrosqualene), mineral oils (petrolatum, isoparaffins, such as isohexadecane, or dioctylcyclohexane), synthetic oils (caprylic/capric triglycerides, isopropyl myristate, cetearyl octanoate, polyisobutylene, ethylhexyl palmitate or alkylbenzoates), volatile silicone oils (cyclomethicone, such as cyclohexamethicone) or nonvolatile silicone oils, and fluorinated oils. Other preferable fatty substances which may be present in the oily phase include, for example, fatty acids such as stearic acid, fatty alcohols such as stearyl alcohol, and waxes.

Preferably, the oily phase of the emulsion can represent from 1 to 50% and better still from 5 to 40% by weight of the total weight of the emulsion. These ranges include all values and subranges therebetween, including 10%, 15%, 20% and 30%.

The aqueous phase of the emulsion or dispersion, which aqueous phase includes at least the organopolysiloxane elastomer particles, is present in the emulsion or dispersion in an amount ranging from 1 to 99% of the emulsion, and more preferably from 5 to 80%, more particularly preferably 10 to 60%, and most preferably from 20 to 50%, based on the total weight of the emulsion. These ranges include all values and subranges therebetween, including 8%, 12%, 25%, 45%, 55%, 65% and 75%.

Preferably, the emulsion includes at least one emulsifying agent to better stabilize the oil/water interface. The emulsifying agent can be chosen from sugar-derived emulsifying agents but can also be composed of amphoteric, anionic, cationic or nonionic surfactants, used alone or as a mixture. These emulsifying agents are appropriately chosen according to the emulsion to be obtained (W/O or O/W).

In a known way, the compositions of the invention can contain adjuvants which are conventional in the cosmetic and dermatological fields, such as hydrophilic or lipophilic active principles, preservatives, antioxidants, fragrances, fillers, coloring materials (pigments or dyes), sun screens and lipid vesicles. These adjuvants are preferably used in the proportions which are usual in the cosmetic or dermatological field, for example from 0.01 to 20% of the total weight of the emulsion, and depending on their nature, they may be introduced into the aqueous phase or into the oily phase of the composition or alternatively into vesicles.

Of course, a person skilled in the art will take care to choose this or these optional additional compounds and/or their amount so that the advantageous properties of the composition according to the invention are not, or not substantially, detrimentally affected by the addition.

Preferable active principles include sun screens; vitamins and in particular vitamins A (retinol), C (ascorbic acid), E (tocopherol), B3 (niacinamide), F and D and their derivatives; unsaturated fatty acids, such as linoleic acid and linolenic acid; α-bisabolol; butters of plant origin mentioned above among the oils, such as shorea butter or karite butter, which reconstitute the skin's lipid barrier and allow the treatment of dry skin; urea; rutin; enzymes; natural extracts, such as green tea, balm extract, thyme extract, procyanidol oligomers (PCO), such as hawthorn PCO, pine PCO and grape PCO; some acids, such as kojic acid, caffeic acid, retinoic acid and its derivatives, or benzene-1,4-di(3-methylidene-10-camphorsulphonic acid); or carotenoids, such as carotenes, such as, for example, α-, β- and γ-carotenes, β, ψ-carotene, ξ-carotene, β, λ-carotene, lycopene (ψ, ψ-carotene) and their mixtures.

Depending on the fluidity of the composition which it is desired to obtain, it is preferable to add one or more gelling agents, such as clays, polysaccharide gums and their derivatives (xanthan gum), carboxyvinyl polymers or carbomers, or polyacrylamides and acrylamide copolymers, such as the product sold under the name of Sebigel 305 by the company Seppic and the product sold under the name Hostacerin AMPS by the company Hoechst (CTFA name: Ammonium polyacryldimethyltauramide). These gelling agents are generally used at concentrations ranging from 0.1 to 10%, preferably from 0.1 to 5% and better still from 0.1 to 3% of the total weight of the composition. These ranges include all values and subranges therebetween, including 0.2%, 0.5%, 1%, 2%, 2.5% and 4%.

Preferable fillers include, for example, polyamide particles and in particular those sold under the name Orgasol by the company Atochem; polyethylene powders; microspheres based on acrylic copolymers, such as those made of ethylene glycol dimethacrylate/lauryl methacrylate copolymer sold by the company Dow Corning under the name of Polytrap; expanded powders, such as hollow microspheres and in particular the microspheres sold under the tradename Expancel by the company Kemanord Plast or under the tradename Micropearl F 80 ED by the company Matsumoto; powders formed of natural organic materials, such as maize, wheat or rice starches, which may or may not be crosslinked, such as starch powders crosslinked with octenylsuccinic anhydride which are sold under the name Dry-Flo by the company National Starch; silicone resin microbeads, such as those sold under the name Tospearl by the company Toshiba Silicone; and their mixtures. Preferably, the fillers may be present alone or in admixture in an amount ranging from 1% to 20%, based on the total weight of the composition, more preferably 3 to 15%, and most preferably 5 to 10%. These ranges include all values and subranges therebetween, including 2%, 4%, 6%, 8%, and 18%.

The compositions according to the invention are particularly suitable for a large number of cosmetic treatments of the skin, lips and hair, including the scalp, in particular for treating, protecting, caring for, removing make-up from and/or cleaning the skin, lips and/or hair. They are also particularly suitable for the treatment of dry skin and/or for dry lips and/or sensitive skin.

The compositions according to the invention are also particularly suitable, for example, as care, make-up removing and/or cleansing products for the face in the form of creams or milks.

A preferred embodiment of the invention is consequently the cosmetic or dermatologic use of the composition as defined above for treating, protecting, caring for, removing make-up from and/or cleaning the skin, lips and/or hair.

Another preferred embodiment of the invention is a process for the cosmetic or dermatologic treatment of the skin, including the scalp, hair and/or lips, characterized in that a composition as defined above is applied to the skin, hair and/or lips.

Another preferred embodiment of the invention is the use of the composition as defined above in the manufacture of a composition intended for caring for dry skin and/or dry lips and/or sensitive skin.

EXAMPLES

Having generally described this invention, a further understanding can be obtained by reference to certain specific examples which are provided herein for purposes of illustration only and are not intended to be limiting unless otherwise specified. The amounts are given as percentages by weight, except where otherwise mentioned.

Example 1

Oil-in-water Emulsion

| Aqueous phase | |
|---|---|
| Glycerol | 5% |
| BY 29-122 (containing 63% of active material) | 5% |
| Preservatives | 0.3% |
| Honey | 0.5% |
| Water | q.s. for 100% |

-continued

| Oily phase | |
|---|---|
| Sucrose palmitate/stearate (Tegosoft PSE from the company Goldschmidt) | 3% |
| Stearic acid | 1% |
| Stearyl alcohol | 3% |
| Liquid petrolatum | 10% |
| Plant perhydrosqualene | 10% |
| Cyclohexamethicone | 5% |
| Gelling agent | |
| Sepigel 305 | 1% |

Procedure: The two phases are heated separately to 70° C. and then the oily phase is dispersed in the aqueous phase with stirring. The gelling agent is subsequently added at a temperature of approximately 60° C.

A smooth, very rich, soft and soothing cream is obtained. Despite the high level of fatty substances, this cream is neither sticky nor greasy.

Example 2

Water-in-oil Emulsion

| Oily phase: | |
|---|---|
| Cetyl dimethicone copolyol (emulsifier) | 1.5% |
| Polyglyceryl-4 isostearate (coemulsifier) | 0.5% |
| Isohexadecane | 5% |
| Cyclohexamethicone | 10% |
| Perhydrosqualene | 10.5% |
| Fillers: | |
| Expancel 551 | 0.5% |
| Crosslinked starch (Dry-Flo) | 2% |
| Aqueous phase: | |
| Glycerol | 5% |
| Magnesium sulphate | 0.5% |
| Fucogel 1000 (from the company Solabia) | 3% |
| Preservatives | 0.4% |
| BY 29-122 (containing 63% of active material) | 5% |
| Water | q.s. for 100% |

Procedure: The fillers are dispersed in the oily phase and then the aqueous phase is dispersed very slowly, with vigorous stirring, in the mixture obtained.

A cream is obtained which is appropriate for caring for dry skin.

Example 3

Water-in-oil Emulsion

| Oily phase: | |
|---|---|
| Isostearylglucoside/isostearyl alcohol (15/85) (i.e. 0.45% of alkylpolyglucoside active material) | 3% |
| Apricot kernel oil | 8% |
| Cyclohexamethicone | 8% |
| Wax | 2% |
| Aqueous phase: | |
| Glycerol | 5% |
| Magnesium sulphate | 0.5% |
| Trehalose | 1% |

-continued

| BY 29-122 (containing 63% of active material) | 5% |
| Preservatives | 0.4% |
| Water | q.s. for 100% |

Procedure: The oily and aqueous phases are heated separately to 75° C. and then the emulsion is prepared by dispersing the aqueous phase in the oily phase with vigorous stirring.

A cream is thus obtained which is smooth, soft and rich on application. It easily penetrates while immediately contributing a soothing nourishing effect. It is particularly appropriate for caring for dry and sensitive skin.

Having now fully described this invention, it will be apparent to one of ordinary skill in the art that many changes and modifications can be made thereto without departing from the spirit or scope of the invention as set forth herein.

This application is based on French patent application 9913990, filed Nov. 8, 1999, the entire contents of which are hereby incorporated by reference, the same as if set forth at length.

What is claimed is:

1. A composition, comprising:
   at least one aqueous phase comprising an aqueous suspension of particles of an at least partially crosslinked organopolysiloxane elastomer; and
   at least one sugar or sugar derivative, wherein said sugar or sugar derivative is selected from the group consisting of sucrose, glucose, galactose, ribose, fucose, trehalose, maltose, fructose, mannose, arabinose, xylose, lactose, alkylated sucrose, alkylated glucose, alkylated galactose, alkylated ribose, alkylated fucose, alkylated trehalose, alkylated maltose, alkylated fructose, alkylated mannose, alkylated arabinose, alkylated xylose, alkylated lactose, natural sugar-containing compounds, honey, polymeric sugars, polymers of fucose, polymers of galactose, polymers of galacturonic acid, and mixtures thereof,
   wherein the organopolysiloxane elastomer is present in an amount sufficient to reduce the sticky feel imparted to skin by the sugar or sugar derivative.

2. The composition according to claim 1, wherein said organopolysiloxane elastomer is obtained by an addition and crosslinking reaction, in the presence of a catalyst, of at least:
   at least one organopolysiloxane (i) having two vinyl groups in the α,ω-position of the silicone chain per molecule; and
   at least one organosiloxane (ii) having at least one hydrogen atom bonded to a silicon atom per molecule.

3. The composition according to claim 2, wherein said organopolysiloxane (i) is an α,ω-dimethylvinylpolydimethylsiloxane.

4. The composition according to claim 1, wherein said aqueous suspension of particles is prepared by a process comprising:
   (a) mixing at least one organopolysiloxane (i) having two vinyl groups in the α,ω-position of the silicone chain per molecule; and
      at least one organosiloxane (ii) having at least one hydrogen atom bonded to a silicon atom per molecule, to obtain a first mixture;
   (b) admixing an aqueous phase comprising at least one emulsifier with said mixture in (a), to obtain a second mixture;
   (c) emulsifying, in said second mixture, said aqueous phase and said first mixture, to obtain an emulsion;
   (d) adding warm water to said emulsion in (c), to form a second emulsion; and
   (e) in said second emulsion, polymerizing said organopolysiloxane (i) and said organosiloxane (ii) in the presence of a platinum group catalyst.

5. The composition according to claim 4, wherein said emulsifier has an HLB value of greater than or equal to 8 and is selected from the group consisting of nonionic, cationic, anionic emulsifiers, and mixtures thereof.

6. The composition according to claim 4, wherein said emulsifier is a nonionic emulsifier.

7. The composition according to claim 1, wherein said particles have a size ranging from 0.1 to 500 μm.

8. The composition according to claim 1, wherein said particles have a Shore hardness of less than or equal to 80.

9. The composition according to claim 1, wherein said particles are present in an amount ranging from 0.1 to 30% by weight with respect to the total weight of the composition.

10. The composition according to claim 1, wherein said sugar or sugar derivative is selected the group consisting of sugar fatty esters, oxyalkylenated sugar fatty esters, polyglycerolated sugar fatty esters, sugar fatty ethers, and mixtures thereof.

11. The composition according to claim 1, wherein said sugar or sugar derivative is selected the group consisting of esters of linear or branched, saturated or unsaturated $C_{12}$ to $C_{22}$ fatty acid and sucrose, maltose, glucose, fructose, mannose, galactose, arabinose, xylose, lactose, trehalose or methylglucose; ethers of $C_8$–$C_{22}$ fatty alcohol and glucose, maltose, sucrose or fructose; and ethers of $C_{14}$–$C_{22}$ fatty alcohol and methylglucose; and mixtures of.

12. The composition according to claim 1, wherein said sugar or sugar derivative is present in an amount ranging from 0.1 to 20% by weight with respect to the total weight of the composition.

13. The composition according to claim 1, further comprising an oily phase.

14. A cosmetic, comprising the composition according to claim 1 and a physiologically acceptable medium.

15. An emulsion selected from the group consisting of an O/W emulsion, W/O emulsion, W/O/W triple emulsion, O/W/O triple emulsion, comprising the composition according to claim 1, an oily phase, and, optionally, one or more emulsifiers.

16. The emulsion according to claim 15, wherein said emulsion is an O/W or a W/O emulsion.

17. The emulsion according to claim 15, wherein said oily phase is present in an amount ranging from 1 to 50% by weight relative to the total weight of the emulsion.

18. A cosmetic, comprising the emulsion according to claim 15 and a physiologically acceptable medium.

19. A method selected from the group consisting of treating, protecting, caring for, removing make-up from, and cleaning the skin, lips or hair, comprising applying the composition according to claim 1 to the skin, lips or hair.

20. A method for treating or caring for at least one selected from the group consisting of dry skin, dry lips, sensitive skin, and combinations thereof comprising applying the composition according to claim 1 to the skin and/or lips.

21. The composition according to claim 1, wherein the composition is an oil-in-water emulsion.

22. The composition according to claim 21, wherein the sugar or sugar derivative is in the oil phase.

23. The composition according to claim 21, herein said particles are present in an amount ranging from 0.9 to 5% by weight with respect to the total weight of the composition.

24. The composition according to claim 21, wherein said sugar or sugar derivative is present in an amount ranging from 1 to 5% by weight with respect to the total weight of the composition.

25. The composition according to claim 1, wherein the composition is a water-in-oil emulsion.

26. The composition according to claim 25, wherein the sugar or sugar derivative is in the water phase.

27. The composition according to claim 25, wherein said particles are present in an amount ranging from 0.9 to 5% by weight with respect to the total weight of the composition.

28. The composition according to claim 25, wherein said sugar or sugar derivative is present in an amount ranging from 1 to 5% by weight with respect to the total weight of the composition.

29. The composition according to claim 1, wherein said particles are present in an amount ranging from 0.2 to 10% by weight with respect to the total weight of the composition.

30. The composition according to claim 1, wherein said particles are present in an amount ranging from 0.9 to 5% by weight with respect to the total weight of the composition.

31. The composition according to claim 1, wherein said sugar or sugar derivative is present in an amount ranging from 0.5 to 10% by weight with respect to the total weight of the composition.

32. The composition according to claim 1, wherein said sugar or sugar derivative is present in an amount ranging from 1 to 5% by weight with respect to the total weight of the composition.

33. A method for preparing an emulsion composition, comprising:

separately heating an oily phase and an aqueous phase, said aqueous phase comprising an aqueous suspension of particles of an at least partially crosslinked organopolysiloxane elastomer and at least one sugar or sugar derivative to obtain a heated oily phase and a heated aqueous phase, wherein said sugar or sugar derivative is selected from the group consisting of sucrose, glucose, galactose, ribose, fucose, trehalose, maltose, fructose, mannose, arabinose, xylose, lactose, alkylated sucrose, alkylated glucose, alkylated galactose, alkylated ribose, alkylated fucose, alkylated trehalose, alkylated maltose, alkylated fructose, alkylated mannose, alkylated arabinose, alkylated xylose, alkylated lactose, natural sugar-containing compounds, honey, polymeric sugars, polymers of fucose, polymers of galactose, polymers of galacturonic acid, and mixtures thereof, wherein the organopolysiloxane elastomer is present in an amount sufficient to reduce the sticky feel imparted to skin by the sugar or sugar derivative;

admixing said heated oily phase and said heated aqueous phase and emulsifying, to obtain said emulsion composition.

34. A method for reducing or eliminating the sticky feel of a composition comprising at least one sugar or sugar derivative, which method comprises introducing into said composition an aqueous suspension of particles of an at least partially crosslinked organopolysiloxane elastomer, wherein said sugar or sugar derivative is selected from the group consisting of sucrose, glucose, galactose, ribose, fucose, trehalose, maltose, fructose, mannose, arabinose, xylose, lactose, alkylated sucrose, alkylated glucose, alkylated galactose, alkylated ribose, alkylated fucose, alkylated trehalose, alkylated maltose, alkylated fructose, alkylated mannose, alkylated arabinose, alkylated xylose, alkylated lactose, natural sugar-containing compounds, honey, polymeric sugars, polymers of fucose, polymers of galactose, polymers of galacturonic acid, and mixtures thereof.

* * * * *

UNITED STATES PATENT AND TRADEMARK OFFICE
CERTIFICATE OF CORRECTION

PATENT NO.     : 6,638,519 B1
DATED          : October 28, 2003
INVENTOR(S)    : Raluca Lorant It is certified that error appears in the above-identified patent and that said Letters Patent is hereby corrected as shown below:

<u>Column 12,</u>
Lines 22 and 27, "selected the" should read -- selected from the --; and
Line 65, "herein" should read -- wherein --.

Signed and Sealed this

Thirteenth Day of January, 2004

JON W. DUDAS
*Acting Director of the United States Patent and Trademark Office*